United States Patent
Webb et al.

(10) Patent No.: US 7,889,931 B2
(45) Date of Patent: Feb. 15, 2011

(54) SYSTEMS AND METHODS FOR AUTOMATED VEHICLE IMAGE ACQUISITION, ANALYSIS, AND REPORTING

(75) Inventors: Sean E. Webb, Suwanee, GA (US); Merritt Franklin Johnson, III, Atlanta, GA (US); Jason D. Watson, Suwanee, GA (US)

(73) Assignee: GB Investments, Inc., Kennesaw, GA (US)

( * ) Notice: Subject to any disclaimer, the term of this patent is extended or adjusted under 35 U.S.C. 154(b) by 1346 days.

(21) Appl. No.: 11/255,642

(22) Filed: Oct. 21, 2005

(65) Prior Publication Data

US 2006/0114531 A1 Jun. 1, 2006

Related U.S. Application Data

(60) Provisional application No. 60/620,988, filed on Oct. 22, 2004.

(51) Int. Cl.
*G06K 9/62* (2006.01)
(52) U.S. Cl. .............. 382/209; 382/141; 382/218; 382/278
(58) Field of Classification Search ............. 382/103, 382/104, 209, 218, 278
See application file for complete search history.

(56) References Cited

U.S. PATENT DOCUMENTS

| | | | |
|---|---|---|---|
| 3,459,203 A | | 8/1969 | Pritchard |
| 4,856,543 A | * | 8/1989 | Petit ................... 134/57 R |
| 5,710,557 A | | 1/1998 | Schuette |
| 5,844,801 A | | 12/1998 | Kodama et al. |
| 6,087,941 A | * | 7/2000 | Ferraz ..................... 340/575 |
| 6,320,654 B1 | | 11/2001 | Alders et al. |
| 6,397,131 B1 | | 5/2002 | Busch et al. |
| 6,630,893 B2 | | 10/2003 | Schuette |
| 6,690,268 B2 | * | 2/2004 | Schofield et al. ............ 340/438 |
| 6,714,831 B2 | | 3/2004 | Matthews et al. |
| 6,747,687 B1 | | 6/2004 | Alves |
| 6,831,996 B1 | | 12/2004 | Williams et al. |
| 6,862,543 B1 | | 3/2005 | Tanimoto et al. |

(Continued)

FOREIGN PATENT DOCUMENTS

DE 100 42 537 A1 3/2002

(Continued)

OTHER PUBLICATIONS

International Search Report in related Application No. PCT/US2005/037848.

(Continued)

*Primary Examiner*—Yosef Kassa

(57) ABSTRACT

The present invention relates to methods, systems, and apparatuses for providing automated vehicle image acquisition, analysis, and reporting. One embodiment of the invention includes a method for providing vehicle damage information to an interested party. The method can include receiving simultaneously captured image data associated with a vehicle. The method can also include comparing at least a portion of the image data with previously stored image data associated with the vehicle. Furthermore, the method can include based at least in part on the comparison of the portion of image data with previously stored image data associated with the vehicle, determining whether damage to the vehicle exists. In addition, the method can include outputting an indicator of whether damage to the vehicle exists.

17 Claims, 7 Drawing Sheets

U.S. PATENT DOCUMENTS

| | | |
|---|---|---|
| 6,895,108 B2 | 5/2005 | Kim |
| 7,075,427 B1 * | 7/2006 | Pace et al. ............. 340/539.22 |
| 7,195,381 B2 * | 3/2007 | Lynam et al. ............... 362/494 |
| 2002/0161533 A1 | 10/2002 | Uegaki |

FOREIGN PATENT DOCUMENTS

| | | |
|---|---|---|
| EP | 1 006 349 A1 | 6/2000 |
| EP | 1 215 612 A1 | 6/2002 |
| EP | 1 464 920 A1 | 10/2004 |
| WO | WO 01/46668 A1 | 6/2001 |

OTHER PUBLICATIONS

Patent Abstracts of Japan, vol. 1999, No. 10, Aug. 31, 1999 & JP 11 144042 A (Harigai Naoki) May 28, 1999 Abstract.

Patent Abstracts of Japan, vol. 1998, No. 03, Feb. 27, 1998 & JP 09 297838 A (Casio Comput. Co. Ltd.) Nov. 18, 1997 Abstract.

* cited by examiner

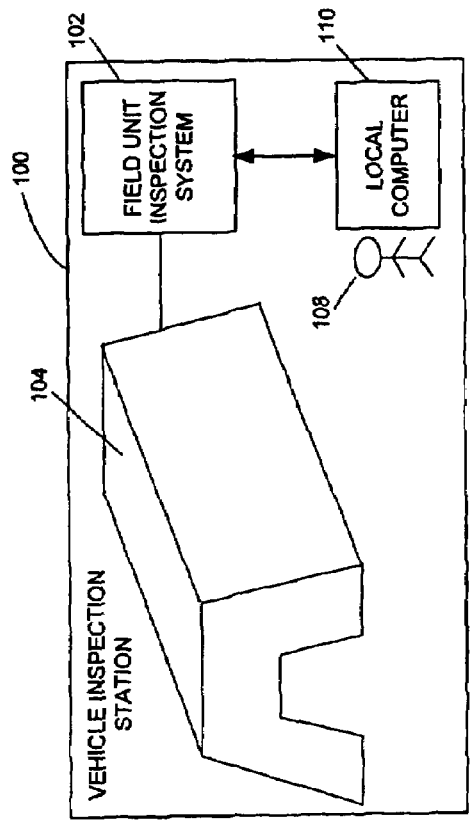
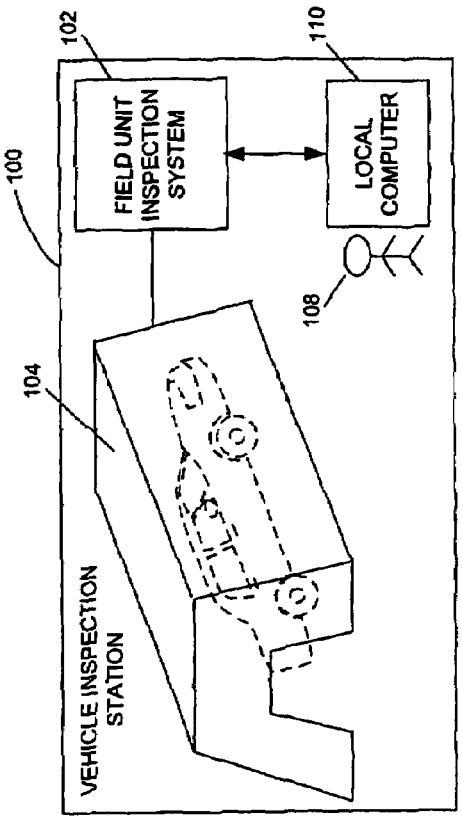
FIGURE 1A
FIGURE 1B

SYSTEMS AND METHODS FOR AUTOMATED VEHICLE IMAGE ACQUISITION, ANALYSIS, AND REPORTING

RELATED APPLICATION

This application claims priority to U.S. Provisional Application Ser. No. 60/620,988, filed Oct. 22, 2004, the contents of which are hereby incorporated by reference.

FIELD OF THE INVENTION

This invention relates generally to the field of vehicle inspection, and more particularly, relates to systems and methods for automated vehicle image acquisition, analysis, and reporting.

BACKGROUND OF THE INVENTION

Conventional systems and processes for inspecting vehicles can utilize images or other vehicle-related information to detect prior damage or repairs. In one type of conventional system, still image cameras can be used to capture images of a vehicle. One type of system used in some parking garage entrances can position a camera adjacent to the parking garage entrance. When a vehicle enters the parking garage entrance, the camera can capture an image of the vehicle. Likewise, when the vehicle exits the parking garage entrance, the camera can capture another image of the vehicle. If needed, images of the vehicle entering and exiting the parking garage can be manually compared by an operator to determine characteristics of the vehicle, such as whether there was any preexisting damage to the vehicle or whether any damage occurred to the vehicle while the vehicle was in the parking garage.

In another conventional system, video cameras can be used to capture video images of a vehicle entering and exiting a parking garage or lot. This type of system can continuously capture video images of a vehicle entering the parking garage or lot. Likewise, when the vehicle exits the parking garage or lot, the system can continuously capture video images of the vehicle exiting parking garage or lot. If needed, images of the vehicle can be manually compared by an operator to determine characteristics of the vehicle, such as whether there was any preexisting damage to the vehicle or whether any damage occurred to the vehicle while the vehicle was in the parking garage or lot.

Manually captured images can be used for advertising a vehicle for sale or for insurance companies performing a damage assessment or inspection to a vehicle. In these processes, a user manually operates and captures images with a camera at different angles with respect to the vehicle. In some instances, a handheld computer device can be utilized during a damage assessment or inspection. Information gathered during the inspection can be input into the computer device for subsequent processing and storage. In these types of processes, a person visually inspects the exterior of the vehicle, identifies any damage visually (sometimes using tools or measuring devices), denotes and characterizes the damage by a series of location codes, and stores the information in the computer device. In some instances, the user can manually operate a camera to capture images of the damage, and associate one or more images with a data record for the vehicle of interest. In these types of processes, the user can collect or otherwise generate graphical representations or descriptions of any damage or repairs. In addition, the interior of the vehicle can also be visually inspected, and the user can input associated data into the handheld computer. Furthermore, components associated with the vehicle, such as the radio, can be functionally tested manually and associated data can be input into the handheld computer. In this manner, these types of information can be processed with a computer and compared to previously stored information or a data record in a database to determine whether additional inspection may be needed.

One conventional system can automate the capture of images associated with a vehicle. This system can include a photo booth to accommodate a vehicle. The photo booth can include several mounted cameras. When a person drives a vehicle into the photo booth, and positions the vehicle with respect to the cameras in the photo booth, lights, photo sensors, or proximity sensors can determine the position of the vehicle and instruct the person when and how to position the vehicle. The user or an operator can then manually operate the cameras in a sequential manner, or an associated computer can operate the cameras in a sequential manner, to capture images of the vehicle. The associated computer can automatically operate the cameras to capture the images in a sequential manner. The operator or driver can then utilize another camera to capture images of the interior of the vehicle.

Other conventional systems can automatically capture images for a variety of uses. In one example, such systems can be used in a process control or defect inspection during a manufacturing process. Such systems can automatically compare an image of a manufactured part to an image or specification for a predefined part. In other examples, such systems can be used in applications, such as medical systems and botany, among others.

Therefore, a need exists for methods, systems, and apparatuses for providing automated vehicle image acquisition, analysis, and reporting.

A further need exists for methods, systems, and apparatuses for providing vehicle damage information to an interested party.

Yet another need exists for methods, systems, and apparatuses for offering a vehicle for sale.

Furthermore, a need exists for methods, systems, and apparatuses for identifying damage to a vehicle and providing damage-related information to an interested party.

SUMMARY OF THE INVENTION

Some or all of the needs can be addressed by embodiments of the present invention. Embodiments of the present invention can capture images of a vehicle, such as an automobile, and can identify various parts of the vehicle for purposes of analysis, comparison, and damage identification. The invention can be used in conjunction with a structure equipped with cameras or other image capturing devices, and associated computing functionality with a database.

Essentially, the invention can provide a system and associated methods for simultaneously capturing images of a vehicle with a series of cameras or other image capturing devices positioned around a target area. In one embodiment, twelve cameras can be mounted to a structure associated with a vehicle inspection station in accordance with the invention. A vehicle can be prompted to enter the structure, and the vehicle is positioned in the target area. The vehicle inspection station can automatically initiate a computer program to activate the cameras or image capturing devices, and simultaneously capture images and image data of various portions of the vehicle within the target area. The images can be transmitted to a vehicle inspection engine and stored in a database or other data storage device. The vehicle can then be prompted to depart the target area and structure.

Embodiments of the invention can also provide an automated review and analysis of images and image data associated with the vehicle. For example, a vehicle inspection engine can compare recent images and image data associated with a vehicle to a stored set of images or image data associated with the vehicle in order to identify potential damage, repairs, or other physical changes to the vehicle. An analysis report can then be generated for transmission to a third party such as a customer, estimator, or an insurance agency. Images, image data, and reports can also be posted to an Internet website for distribution or access by a third party accessing the website via a network.

One embodiment of the invention can include a method for providing vehicle damage information to an interested party. The method can include receiving simultaneously captured image data associated with a vehicle. In addition, the method can include comparing at least a portion of the image data with previously stored image data associated with the vehicle. Furthermore, the method can include determining whether damage to the vehicle exists based at least in part on the comparison of the portion of image data with previously stored image data associated with the vehicle. Further, the method can include outputting an indicator of whether damage to the vehicle exists.

Another embodiment of the invention can include a method for offering a vehicle for sale. The method can include receiving identification data associated with a vehicle. The method can also include receiving simultaneously captured image data associated with the vehicle. In addition, the method can include transmitting a communication comprising at least a portion of the identification data associated with the vehicle and at least a portion of the image data associated with the vehicle, wherein the communication offers the vehicle for sale to a consumer.

Yet another embodiment of the invention can include a system for identifying damage to a vehicle and providing damage-related information to an interested party. The system can include a plurality of image capturing devices capable of simultaneously capturing image data of a vehicle. In addition, the system can include a vehicle inspection engine capable of receiving from the plurality of image capturing devices simultaneously captured image data associated with the vehicle. Furthermore, the vehicle inspection engine can be capable of comparing at least a portion of the image data with previously stored image data associated with the vehicle. Furthermore, the vehicle inspection engine can be capable of determining whether damage to the vehicle exists based at least in part on the comparison of the image data with previously stored image data associated with the vehicle. Further, the vehicle inspection engine can be capable of outputting an indicator of whether damage to the vehicle exists.

Another aspect of the invention can include a computer-readable medium containing program code. The program code can be adapted to receive simultaneously captured image data associated with a vehicle. In addition, the program code can be adapted to compare at least a portion of the image data with previously stored image data associated with the vehicle. Furthermore, the program code can be adapted to determine whether damage to the vehicle exists based at least in part on the comparison of the portion of image data with previously stored image data associated with the vehicle. Further, the program code can be adapted to output an indicator of whether damage to the vehicle exists.

Other embodiments of methods, systems, and apparatuses according to the invention are apparent from the following detailed description of the disclosed embodiments and the appended drawings and claims.

BRIEF DESCRIPTION OF THE DRAWINGS

FIGS. 1A and 1B illustrate an example of a process flow and environment in which an exemplary single vehicle inspection station and processes can operate in accordance with an embodiment of the invention.

DETAILED DESCRIPTION OF EMBODIMENTS

Figure 2:
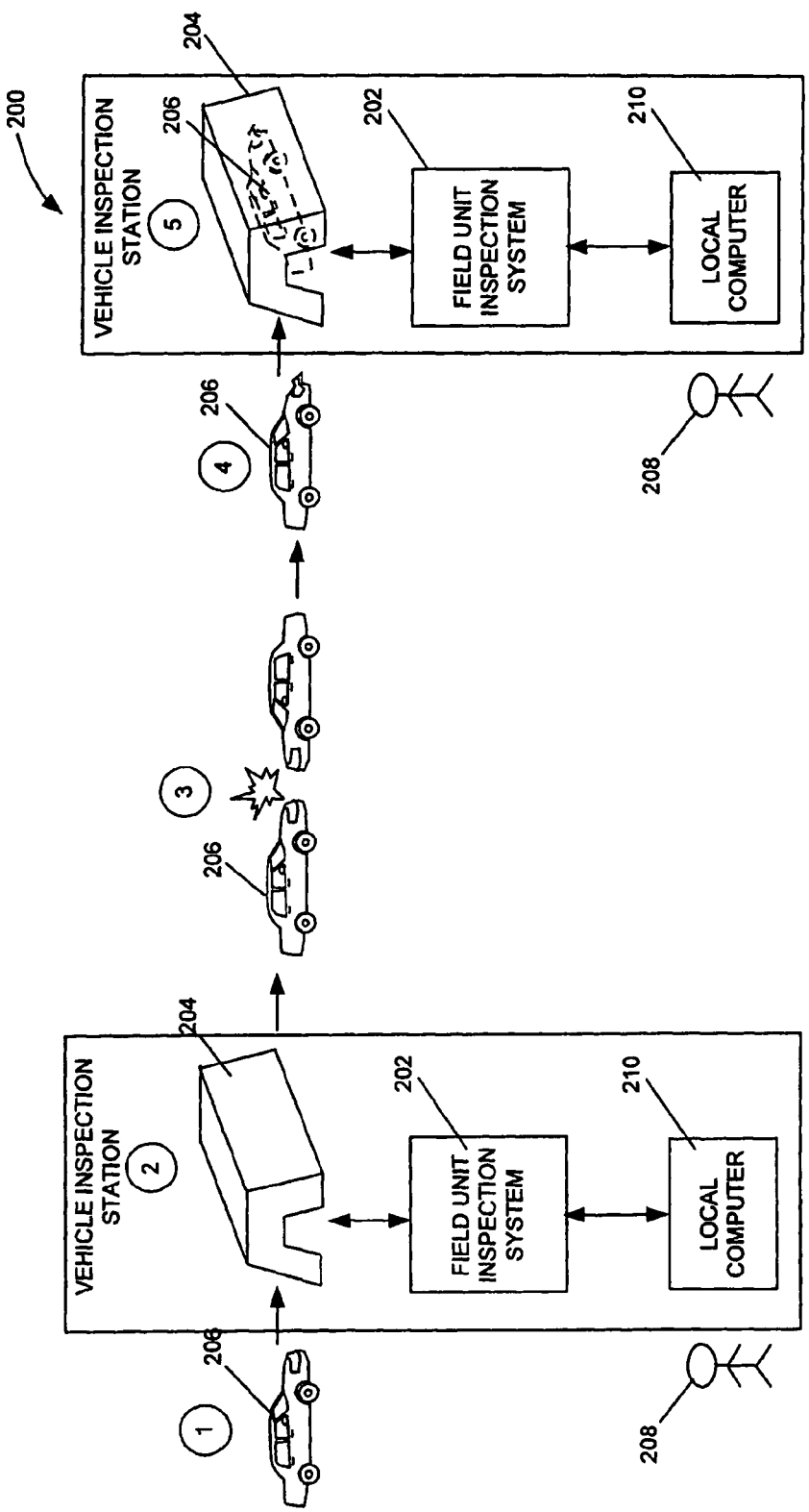
FIG. 2 illustrates another example of a process flow and an environment in which an exemplary single vehicle inspection station and processes can operate in accordance with an embodiment of the invention.

Various embodiments of the invention address some or all of the above issues and combinations thereof. They do so by providing methods, systems, and apparatuses for automated vehicle image acquisition, analysis, and reporting.

"Image data" may include any image or data related to an image or visual representation of a physical characteristic of an object. Examples of image data can include, but are not limited to, a still image, a video frame, or data representing a visual physical characteristic of an object, such as a vehicle. Image data can be received from or otherwise collected by a camera, a video camera, or an image capturing device.

The term "identification data" may include, but is not limited to, a vehicle identification number, a license plate, a dealer tag, vehicle-related data from a radio frequency identification device, vehicle-related data from a bar code, a vehicle make, a vehicle model, or a vehicle year of manufacture. Identification data may also include other types of suitable data known to those skilled in the art.

The phrase "simultaneously captured image data" may include at least one image or image data received or obtained substantially contemporaneously with another image or image data. Examples of "simultaneously captured image data" can include at least two images captured at the same instance of time, at least two frames captured at the same time, at least two images captured nearly at the same time, at least two frames captured nearly at the same time, at least two images captured during overlapping periods of time, at least two frames captured during overlapping periods of time. Simultaneously captured image data may also include other types of suitable data known to those skilled in the art.

The term "damage" may include damage occurring by collision with an object, such as with a vehicle. The term can also include damage or physical changes which may occur over time. Furthermore, the term can include a repair of prior damage, or any other change to a physical characteristic of a vehicle.

Embodiments of the invention can be implemented as a field inspection station. A field inspection station can be a stand alone unit or system, or can be networked with other field inspection stations and/or a server and database.

FIGS. 1A and 1B show a process flow for a single vehicle inspection station in accordance with various embodiments of the invention. By way of example, the process and system in accordance with embodiments of the invention can operate in a variety of environments, such as an enclosure, a parking lot, a predefined space, an open space, or any combination therein. One example of an environment in which some or all components of a system in accordance with embodiments of the invention can operate is a vehicle inspection station 100 shown in FIGS. 1A and 1B. A vehicle inspection station 100 is capable of imaging, managing, and tracking vehicle-related information, such as vehicle damage and/or repair information. In one embodiment, a vehicle inspection station 100 includes a field unit inspection system 102, an enclosure or portable structure 104, and a local computer 110. The field unit vehicle inspection system 102 can image, manage, and track damage and/or repair information on personal, commercial and/or fleet-type vehicles, such as cars, trucks, or other motorized or non-motorized vehicles. Examples of various components and associated functionality of the field unit inspection system 102 in accordance with an embodiment of the invention are shown and described with respect to FIG. 3. For instance, components associated with a field unit inspection system 102 can be image data or collection equipment such as image capturing devices, computers, at least one position sensor, and at least one guide device or traffic control indicator. The field unit inspection system 102 may be networked with other vehicle inspection stations and/or centralized computers, servers, and databases. One example of a suitable system is the Agrios Automated Damage Archival System, which is designed and distributed by Agrios, Inc. of Atlanta, Ga., the assignee of this application.

The enclosure or protective structure 104 is capable of housing or otherwise protecting some or all components associated with a field unit inspection system 102. The structure 104 can be large enough for a vehicle of interest to drive into, stop, and drive through. An example of a suitable structure for a field unit inspection system, such as 102, is a portable or permanent garage-type or carport type structure, also known as a field unit.

The field unit inspection system 102 is adapted to perform various image acquisition, analysis, and reporting techniques, routines, and processes, including simultaneously capturing image data associated with a vehicle. The field unit inspection system 102 can include various components including a series of image capturing devices, at least one position sensor, at least one guide device, and a vehicle identification device. These and other associated components and their related functionality are described in greater detail in FIG. 3.

FIGS. 1A and 1B show a vehicle, such as 106, in the vehicle inspection station 100. In FIG. 1A, the vehicle 106 can approach and enter the structure 104 of the vehicle inspection station 100. In FIG. 1B, the vehicle 106 is shown adjacent to or within the structure 104. While the vehicle 106 is adjacent to or within the structure 104, the field unit inspection system 102 can perform various image acquisition, analysis, and reporting techniques, routines, and processes. Embodiments of such image acquisition, analysis, and reporting techniques, routines, and processes are described in greater detail below in FIGS. 3 and 4. In the embodiment shown, the field unit inspection system 102 can obtain simultaneously captured image data associated with the vehicle 106. If necessary, the vehicle inspection system 102 can provide images, analysis, or reports to a user, such as 108, via a local computer, such as 110. In other embodiments, the vehicle inspection station 100 is connected to a network, such as the Internet, and can provide reports to a client device. Other aspects, components, and functionality of a field unit inspection system in accordance with embodiments of the invention are further described in FIGS. 2 through 7.

FIG. 2 shows another process flow for a system in accordance with various embodiments of the invention. The environment 200 shown in FIG. 2 is another field-type environment 200 in which some or all components of a system in accordance with embodiments of the invention can operate. Some or all of the steps or processes described in steps 1 through 5 in FIG. 2 can be repeated as necessary.

The environment in FIG. 2 also includes a vehicle inspection station 201, which includes a field unit inspection system 202, and a structure 204, similar to like elements 102, 104 shown in FIGS. 1A and 1B. The first and second steps shown in FIG. 2 as "1" and "2" are similar to the processes described in FIGS. 1A and 1B respectively. As shown in step "2", while a vehicle 206 is adjacent to or within the structure 204, the field unit inspection system 202 can perform various image acquisition, analysis, and reporting techniques, routines, and processes, including obtaining simultaneously captured image data associated with the vehicle 206. Such image acquisition, analysis, and reporting techniques, routines, and processes are described in greater detail below in FIGS. 3 and 4.

In the third step, shown as "3", the vehicle 206 experiences damage. In this instance, the vehicle collides with another vehicle. In other instances, damage can include any change to a physical characteristic of a vehicle.

In the fourth step, shown as "4", the vehicle 206 can approach and enter the structure 204 associated with the vehicle inspection station 201, or can approach and enter a different vehicle inspection station that is associated via a network with one or more vehicle inspection stations that include the vehicle inspection station 201.

In the fifth step, shown as "5", the vehicle 206 is shown adjacent to or within the structure 204. Similar to FIG. 1B and step "2" in FIG. 2, while the vehicle 206 is adjacent to or within the structure 204, the field unit inspection system 202 can perform various image acquisition, analysis, and reporting techniques, routines, and processes, including obtaining simultaneously captured image data associated with the vehicle 206. Such image acquisition, analysis, and reporting techniques, routines, and processes are described in greater detail below in FIGS. 3 and 4.

Based at least in part on a comparison between some or all simultaneously captured image data associated with the vehicle 206 obtained in step "2" and simultaneously captured image data associated with the vehicle 206 obtained in step "5," the field unit inspection system 202 can determine whether damage exists to the vehicle 206. If necessary, the field unit inspection system 202 can provide images, analysis, or reports to a user, such as 208, via a local computer, such as 210. Other aspects, components, and functionality of a vehicle inspection system in accordance with embodiments of the invention are further described in FIGS. 3 through 7.

Figure 3:
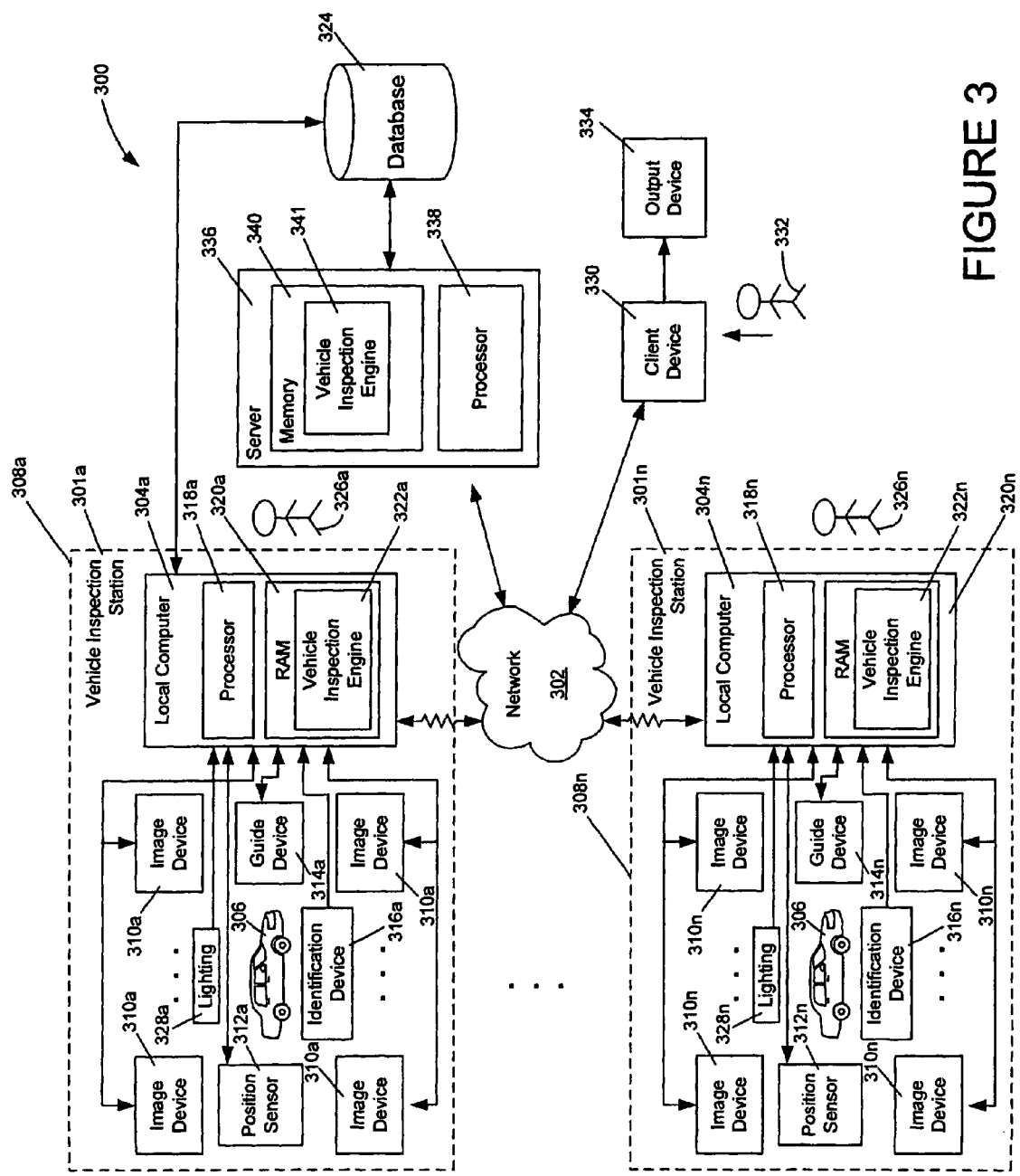
FIG. 3 illustrates an exemplary system in accordance with an embodiment of the invention.

FIG. 3 is an exemplary system in accordance with various embodiments of the invention. The field unit inspection system 300 shown is by way of example, and the system 300 can operate in a variety of environments, such as an enclosure, a parking lot, a predefined space, or an open space such as a field. Examples of field environments are shown in FIGS. 1A, 1B, and 2.

Referring back to FIG. 3, a field unit inspection system 300 is shown with a communications network 302 in communication with at least one local computer 304a of a vehicle inspection station 301a. A vehicle 306 of interest is shown in FIG. 3 adjacent to a structure or field unit 308a associated with the vehicle inspection system 300. The local computer 304a can be located adjacent to or within a structure or field unit 308a, and can be in communication with various inspection components including, for example, a series of image capturing devices 310a, at least one position sensor 312a, at least one guide device 314a, a vehicle identification device 316a, and lighting 328a. Any number of other vehicle inspection stations 301n can also be in communication with the network 302. Other local computers 304n can also be located adjacent to or within a respective structure or field unit, such as 308n, associated with the vehicle inspection system 300. In addition, such local computers 304n can be in communication with various respective inspection components including a series of image capturing devices 310n, at least one position sensor 312n, at least one guide device 314n, a vehicle identification device 316n, and lighting 328n.

In some embodiments, any number of inspection components, such as the series of image capturing devices 310a-n, position sensors 312a-n, guide devices 314a-n, vehicle identification devices 316a-n, and lighting 318a-n may be in direct communication with the network 302 without communication via a local computer, such as 304a-n. In this manner, any number of such inspection components or vehicle inspection stations, such as 301a-n, can be networked with other vehicle inspection stations and/or centralized computers, servers, and databases. For example, in the embodiment shown in FIG. 3, the vehicle inspection system 300 can include a server 336 and a database 324. The server 336 and database 324 can be in communication with one or more vehicle inspection stations 301a-n via the network 302. Centralized server control and operation of some or all inspection components, as well as centralized data storage, associated with any number of vehicle inspection stations can be achieved in a network configuration. Other embodiments can include any number of inspection components, vehicle inspection stations such as 301a-n, servers such as 336 and/or databases such as 324 in communication with each other via a network such as 302.

The communications network 302 shown in FIG. 3 can be a wireless communications network capable of transmitting both voice and data signals, including image data signals or multimedia signals. For example, the network 302 can be the Internet. Other types of communications networks can be used in accordance with various embodiments of the invention.

In one embodiment, the server 336 can be in communication with a network, such as 302 or the Internet. Similar to the local computers 304a-n, the server device 336 shown comprises a processor 338 coupled to a computer-readable memory 340. A vehicle inspection engine, such as 341, or other computer-executable instructions can be stored and executed by the server 336. The server device 336 can be in communication with a database, such as 324, or other data storage device. The database 334 can receive and store data from the server 334, or from a local computer, such as 304a, via the network 302. Data stored in the database 324 can be retrieved by the server 334 or local computers 304a-n as needed.

The server 334 can transmit and receive signals and information to and from multiple sources via the network 302, including a local computer such as 304a, image capturing devices such as 310a-n, position sensors such as 312a-n, guide devices such as 314a-n, identification devices such as 316a-n, lighting 328a-n, and a database such as 324 or other data storage device.

In one embodiment, a database can be a postgress relational database. In another embodiment, a database can be any suitable SQL-type database.

Server device 336, depicted as a single computer system, may be implemented as a network of computer processors. Examples of a suitable server device are servers, mainframe computers, networked computers, a processor-based device, and similar types of systems and devices. Client processors 318a-n and the server processor 338 can be any of a number of computer processors, such as processors from Intel Corporation of Santa Clara, Calif. and Motorola Corporation of Schaumburg, Ill. The computational tasks associated with rendering the graphical image could be performed on the server device(s) and/or some or all of the local computer(s).

Each local computer 304a-n shown in FIG. 3 can be a computer or processor-based device capable of communicating with the communications network 302 via a signal, such as a wireless frequency signal or a direct wired communication signal. Each local computer, such as 304a, can include a processor 318a and a computer-readable medium, such as a random access memory (RAM) 320a, coupled to the processor 318. The processor 318a can execute computer-executable program instructions stored in memory 320a. Computer executable program instructions stored in memory 320a can include a vehicle inspection application program, or vehicle inspection engine 322a. Aspects and functionality of a vehicle inspection engine 322a are described in detail below.

Suitable processors for a local computer 304a-n may comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media include, but are not limited to, an electronic, optical, magnetic, or other storage or transmission device capable of providing a processor, such as the processor 318a, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

As shown in FIG. 3, a memory 320a, a database 324, or other data storage devices can store image data associated with a vehicle for subsequent retrieval and processing. Information associated with a position of a vehicle and instructions associated with guiding a driver or operator of a vehicle can also be stored in a memory such as 320a, database such as 324, or other data storage device. In this manner, simultaneously captured images associated with a vehicle obtained by a series of image capturing devices, position information associated with a vehicle and collected by one or more position sensors, and one or more instructions associated with one or more guide devices can be stored for subsequent retrieval and processing.

The memory 320a or database 324 can be in communication with other databases, such as a centralized database, or other types of data storage devices. When needed, data stored in the memory 320a or database 328 may be transmitted to a centralized database capable of receiving data, information, or data records from more than one database or other data storage devices.

Local computers 304a-n may also comprise a number of external or internal devices such as a mouse, a CD-ROM, DVD, a keyboard, a display, or other input or output devices. Examples of local computers 304a-n are personal computers, mobile computers, handheld portable computers, digital assistants, personal digital assistants, cellular phones, mobile phones, smart phones, pagers, digital tablets, desktop computers, laptop computers, Internet appliances, and other processor-based devices. In general, a local computer, such as 304a, may be any type of processor-based platform that is connected to a network, such as 302, and that interacts with one or more application programs. Local computers 304a-n may operate on any operating system capable of supporting a browser or browser-enabled application, such as Microsoft® Windows® or LINUX. The local computers 304a-n shown include, for example, personal computers executing a browser application program such as Microsoft Corporation's Internet Explorer™, Netscape Communication Corporation's Netscape Navigator™, and Apple Computer, Inc.'s Safari™. In one embodiment, the local computers can operate with the LINUX operating system.

In one embodiment, suitable local computers can be standard desktop personal computers with Intel x86 processor architecture, operating a LINUX operating system, and programmed using a Java language.

In some embodiments, a local computer, such as 304a, can be in communication with an output device (not shown), such as a display screen. Various output can be obtained via an associated output device including image data, vehicle-related information, or other information associated with a vehicle. In such embodiments, a user, such as 326a, can interact with a local computer, such as 304a, via an input device (not shown) such as a keyboard or a mouse. For example, a user 304a can manually input information, such as loading image data associated with a vehicle, such as 306, or inputting other vehicle-related information or information associated with a vehicle 306, via the local computer 304a. In another example, a user, such as 326a can input vehicle-related information via the local computer 304a by keying text via a keyboard or inputting a command via a mouse. In another example, a user, such as 326a, can input position information associated with a vehicle via the local computer 304a by entering data via a keyboard or other input device. In yet another example, a user, such as 326a, can input an instruction for a driver or operator of a vehicle 306 via the local computer 304a by entering data via a keyboard or other input device.

In one embodiment, suitable local computers can utilize USB-type connections and a USB2-type hub component that can multiplex multiple, concurrent USB1-type data streams. In this configuration, multiple types and combinations of data or instructions to or from inspection devices such as position sensors, image capturing devices, guide devices, vehicle identification devices, and lighting can be transmitted to one or more local computers, and then transmitted via a network to a vehicle inspection engine, such as 322. In this manner, data from any number of such inspection components, including position sensors, image capturing devices, guide devices, vehicle identification devices, and lighting, can be transmitted to other vehicle inspection stations and/or centralized computers, servers, and databases. For example, in the embodiment shown in FIG. 3, some or all of the image capturing devices 310a-n, position sensors 312a-n, guide devices 314a-n, identification devices 316a-n, and lighting 328a-n can transmit or receive information or instructions to a server such as 336 and/or database such as 324 for subsequent storage and processing.

In the embodiment shown, at least one position sensor, such as 312a, can detect a position associated with a vehicle adjacent to or within a structure or field unit such as 308a. In one embodiment, one or more position sensors capable of providing position information associated with a vehicle can communicate with a local computer such as 304a, and communicate such information to a vehicle inspection engine such as 322a for subsequent processing. For example as shown in FIG. 3, at least one position sensor 312a can communicate position information associated with a vehicle to a local computer 304a, and the vehicle inspection engine can process the position information. In some instances, a position sensor may communicate position information directly to a network, such as 302, and communicate such information to a server such as 336 and/or database 324. In any of these instances, at least one position sensor is capable of providing position information associated with a vehicle to a vehicle inspection engine, such as 322a, or to a remote location, such as a remote client or server device via a network, such as 302.

One suitable position sensor is an optical positioning sensor capable of providing a signal associated with a position of an adjacent vehicle. An example of another suitable position sensor is an infrared (IR)-type beam detector. Other types of position sensors can include, but are not limited to, ultrasound, or any other process or device capable of providing or sensing a position of an adjacent vehicle.

In the embodiment shown, at least one guide device, such as 314a, can provide at least one instruction to a driver or operator of a vehicle adjacent to or within a structure or field unit such as 308a. In one embodiment, one or more guide devices can communicate with a local computer, such as 304a, to receive a signal associated with an instruction for a driver or operator of a vehicle, wherein the signal was generated and transmitted by a vehicle inspection engine, such as 322a. For example, as shown in FIG. 3, at least one guide device 314a can communicate with local computer 304a to receive a signal associated with an instruction for a driver or operator of a vehicle, such as 306, wherein the signal is generated and transmitted by the vehicle inspection engine 322a. In other instances, a guide device, such as 314a, may receive at least one instruction or related signals directly from a network, such as 302, which may receive such information from a server such as 336 and/or database 324. In any of these instances, a guide device capable of providing an instruction to a driver or operator associated with a vehicle can communicate or otherwise receive instruction information from a vehicle inspection engine 322a, or from a remote location, such as from a remote client or a server, via a network, such as 302.

One or more vehicle identification devices such as 316a can be mounted to or adjacent to the field unit 308a. Some or all of the vehicle identification devices 316a can transmit respective signals with vehicle identification information to the vehicle inspection engine 322a while the vehicle 306 is adjacent to or within the field unit 308a. Based at least in part on the vehicle identification information, the vehicle inspection engine 322a can identify the vehicle 306. In some instances, a vehicle of interest may be identified as "new vehicle to the system" and the vehicle inspection engine 322a can generate a data record or other data with the vehicle identification information for storage in memory such as 320a, a database such as 324, or data storage device. In other instances, a vehicle of interest may be identified as a "return vehicle to the system," and the vehicle inspection engine 322a can retrieve corresponding data records or other data with any previously stored or prior vehicle identification information from a memory such as 320*a*, a database such as 324, or a suitable associated data storage device.

In one embodiment, image data from an image capturing device, such as 310*a*, or camera can be processed by a vehicle inspection engine, such as 322*a*, to identify a vehicle. Such processing can utilize an optical character recognition (OCR) technique, process, software, or device capable of identifying a vehicle license tag identification number or vehicle identification number (VIN). In some instances, a vehicle inspection engine 322*a* can communicate with a database, such as 324, or other data storage device to reference and search previously stored license tag identification numbers or vehicle identification numbers.

In another embodiment, a vehicle, such as 306, can be identified by reading a radio frequency identification device (RFID) tag or a bar code mounted to the vehicle. In some instances, a vehicle inspection engine, such as 322*a*, may communicate with a memory such as 320*a*, a database such as 324, or other data storage device to reference and search previously stored radio frequency identification device (RFID) tags or bar codes.

In yet another embodiment, a company-specific form of vehicle identification can be used to identify a vehicle. Edge detection techniques, processes, software, or devices can be utilized to identify a particular vehicle by its physical characteristics. Physical characteristics can include, but are not limited to, exterior surfaces, joints, and edges associated with a vehicle. In some instances, a vehicle inspection engine, such as 322*a*, may communicate with a memory 320*a*, a database such as 324, or other data storage device to reference and search previously stored or otherwise known information from a vehicle information database to determine the make, model, and year of the vehicle of interest.

In the embodiment shown in FIG. 3, a series of image capturing devices 310*a* are shown associated with a local computer 304*a* and vehicle inspection engine 322*a*. Each of the image capturing devices 310*a* can provide image data associated with a vehicle positioned adjacent to the image capturing devices 310*a*. Each of the image capturing devices 310*a* shown can be in communication with a local computer, such as 304*a*, and vehicle inspection engine 322*a*. Image capturing devices, such as 310*a*, capable of providing vehicle-related image information can also be in communication with any number of other local computers 304*n*, and vehicle inspection engines 322*n*. In other instances, one or more image capturing devices capable of obtaining image data associated with a vehicle may communicate image data directly to a network, such as 302, a server such as 336, a database such as 324, or a vehicle inspection engine such as 341 associated with a server such as 336.

Some or all of the image capturing devices, such as 310*a*, can be adapted to mount to the structure or a field unit, such as 308*a*. The field unit 308*a* can include guard rails on the each side of the field unit adjacent to a vehicle, such as 306, in or adjacent to the field unit 308*a*. In addition, guard rails can be located above and in any location around or adjacent to a vehicle 306 in or adjacent to the field unit 306. In some embodiments, any shape or configuration of camera or image capturing device mounting can be used with a field unit 308*a* or any other structure associated with a vehicle inspection system. In some embodiments, one or more cameras or image capturing devices can be installed on moving fixtures, armatures, or robot-like automation devices.

A suitable image capturing device capable of providing image data associated with a vehicle or other vehicle-related image information can be a digital camera. Examples of suitable image capturing devices are Canon A75, A85, and A520 cameras, or any other consumer-type USB-connected Canon brand cameras. In one embodiment, suitable cameras can be in communication with a vehicle inspection engine, such as 322*a*, via a USB-connection or via an Ethernet-type connection. Other types of devices and technologies capable of providing image data associated with a vehicle or vehicle-related image information associated with a vehicle can be used with other embodiments of the invention, including, but not limited to, a camera, video camera, a visible light camera, x-ray camera, infrared camera, laser sensor, radar sensor, and electrostatic sensor.

In other embodiments, image capturing devices can utilize various combinations of sensors or cameras that use visible light, x-ray, infrared, or any combination of wavelength of electromagnetic waves. In some instances, multiple camera images or image data associated with a vehicle can be merged to provide three-dimensional shape of a surface associated with a vehicle of interest. For example, in one embodiment, laser-type or radar-type sensors can be used to simultaneously capture image data associated with a shape of an external surface of a vehicle. In another embodiment, electrostatic-type sensors can be used to simultaneously capture image data associated with a shape of an external surface of a vehicle.

In some embodiments, camera or image capturing device characteristics can be controlled by a vehicle inspection engine such as 322*a*, for instance, camera image resolution, lens characteristics, lens filtering. In addition, the placement of some or all cameras or image capturing devices can be varied by the vehicle inspection engine 322 to obtain images of virtually any size, angle, or field of view of the vehicle of interest.

In some embodiments, lighting, such as 328*a*, can be utilized in conjunction with the operation of image capturing devices, such as 310*a*, and can be controlled by a vehicle inspection engine, such as 322*a*. For example, commercially available lighting (fixed or flash) can be mounted to a structure associated with a vehicle inspection system, such as 322*a*. A vehicle inspection engine, such as 322*a*, can be in communication with the lighting 328*a* to control the amount, intensity, or other lighting characteristics. In some instances, lighting such as 328*a* can be controlled based on the position of a vehicle, the time of day, or the amount of light detected at a particular time. As necessary, position information from at least one position sensor 310*a*, or from other types of sensors, such as light sensors, can be utilized by a vehicle inspection engine, such as 322*a*, to operate and control any lighting, such as 328*a*, which may also be associated with the operation, control, or effect of some or all associated image capturing devices, such as 310*a*.

In another embodiment, image data associated with a vehicle's exterior, interior, undercarriage, wheels, and tires can be captured, archived, assessed, and compared by a vehicle inspection engine, such as 322*a*. In some embodiments, image data associated with a vehicle's consumable-type parts, such as tire tread, windshield wipers, headlamps, and the like, can be captured, archived, assessed, and compared by a vehicle inspection engine, such as 322*a*.

In another embodiment, image capturing devices can capture simultaneously captured image data associated with a vehicle while the vehicle is still in motion or otherwise moving. In other embodiments, image capturing devices can capture simultaneously captured image data associated with a vehicle while the vehicle is stopped or otherwise not in motion.

As discussed above, various system components such as image capturing devices 310a, position sensors 312a, guide device 314a, vehicle identification devices 316a, and other components associated with a vehicle inspection system can be controlled and operated by a vehicle inspection engine, such as 322a, operating on a local computer 304a, vehicle inspection station 301a, or server 336, or combination thereof. For example, in one embodiment, a vehicle inspection engine, such as 322a, can coordinate respective signals from one or more associated position sensors and guide devices to provide a set of instructions to a driver or operator of a vehicle to enter and exit a structure or field unit, such as 306a. For example, one or more position sensors 312a can detect a vehicle, such as 306, adjacent to or within a structure or field unit 308a, and corresponding signals can be transmitted to the vehicle inspection engine 322a. The vehicle inspection engine 322a can determine whether the vehicle 306 is sufficiently positioned with respect to the structure or field unit 308a, and whether the vehicle 306 is sufficiently positioned to the image capturing devices 310a. When the vehicle 306 is sufficiently positioned with respect to the structure or field unit 308a, or to the image capturing devices 310a, the vehicle inspection engine 322a can send a respective signal to trigger or otherwise activate one or more guide devices 314a to provide at least one instruction to the driver or operator of the vehicle 322a.

In one example, when a vehicle inspection engine 322a receives a signal from at least one position device 312a that a vehicle 306 is adjacent to or within a structure or field unit, such as 308a, the vehicle inspection engine 322a can send a signal to at least one guide device 314a, such as a traffic control indicator. The guide device 314a can notify the driver or operator of the vehicle when to stop the vehicle 306 with respect to the structure or field unit 308a. For instance, a guide device 314a such as a traffic control indicator can alternate between a green light, indicating move or go, and a red light, indicating not to move or stop.

In another example, a vehicle inspection engine, such as 322a, can receive position information from at least one position sensor, such as 312a, located adjacent to a vehicle, such as 306. Based at least in part on the position information, the vehicle inspection engine 322a can provide at least one instruction capable of guiding a driver of the vehicle 306. An instruction can be provided by at least one guide device, such as 314a. In this example, the vehicle inspection engine 322a can provide interactive functionality to prompt the driver of the vehicle 306 to sufficiently position a vehicle with respect to the structure or field unit 308a, or with respect to a series of image capturing devices 310a. Upon receipt of real time position information from at least one position sensor 312a, the vehicle inspection engine 322a can provide a series of instructions or other feedback via at least one guide device 314a to permit a driver of a vehicle 306 to enter or move, as needed, adjacent to the field unit 308a, and to stop the vehicle 306, as needed, when the vehicle is sufficiently located adjacent to the image capturing devices 310a. When the vehicle 306 is sufficiently located with respect to the image capturing devices 310a, the vehicle inspection engine 322a can simultaneously capture image data associated with the vehicle 306.

In one embodiment, a vehicle inspection engine, such as 322a, can identify a vehicle. As a vehicle, such as 306 moves adjacent to or within a structure or field unit, such as 308a, at least one vehicle identification device, such as 316a, can be automatically or manually operated to obtain vehicle identification information from the vehicle 306 or from a device or signal associated with the vehicle 306. In one example, a vehicle inspection engine 322a can receive a signal from at least one vehicle identification device 316a, such as a bar code reader or RFID tag reader.

In another embodiment, other vehicle-related information, such as a VIN number or physical characteristics, can automatically or manually be collected or otherwise received by the vehicle inspection engine, such as 322a, from a user or by one or more sensors or other data collection devices, techniques, or methods. In any instance, such vehicle-related information can be transmitted to the vehicle inspection engine 322a, and stored in memory 320a, a database such as 324, or other data storage device for subsequent retrieval or processing.

In one embodiment, the vehicle inspection engine 322a can simultaneously trigger or otherwise activate the image capturing devices 310a positioned adjacent to the vehicle 306. The vehicle inspection engine 322a can store the image data in memory 320a, a database such as 328, or other data storage device for subsequent retrieval or processing.

In one embodiment, the series of image capturing devices can be twelve cameras mounted at twelve different positions with respect to a vehicle adjacent to or within a structure or field unit associated with a vehicle inspection system, such as 300. An example of a suitable arrangement for a series of image capturing devices is shown and described in FIG. 5.

In one embodiment, the vehicle inspection engine 322a can simultaneously upload image data from some or all of the image capturing devices 310a, and store the image data in memory 320a, or an associated database such as 324, or data storage device. After simultaneously captured image data is received, the vehicle inspection engine 322a can then send a respective signal to trigger or otherwise activate one or more guide devices 314a to provide at least one instruction to the driver or operator of the vehicle 306. For example, a vehicle inspection engine 322a can send a signal to at least one guide device 314a, such as a traffic control indicator, and the guide device 314a can notify the driver or operator of the vehicle 306 to exit the structure or field unit, such as 306a.

In another embodiment, a vehicle can be sufficiently positioned with respect to the field unit 306a, or to the image capturing devices 308a, while the vehicle remains in motion with respect to the field unit 306a, or to the image capturing devices 308a. In these instances, the image capturing devices 308a can simultaneously capture of image data associated with the moving vehicle. A vehicle inspection engine, such as 322a, may provide feedback or other instructions to a driver or operator of the moving vehicle via associated guide devices, such as 314a, based at least in part on the position or speed of the vehicle obtained or otherwise derived from one or more position sensors, such as 312a.

In one embodiment, the image inspection engine 322a can compare previously stored or captured image data of the same vehicle against gold standard-type image data of the same make, model, and year of the vehicle of interest. Image comparison techniques, processes, software, or devices can be used by the image inspection engine 322a to analyze and compare image data. Based on the image data comparison, image analysis, differential techniques such as surface and/or thermal imaging techniques, or other machine vision techniques can be utilized to assess identified areas of potential damage, repair, or physical change. In some instances, additional functionality can assess, quantitatively or qualitatively, the type of damage, repair, or physical change to the vehicle. In this manner, such assessments can be used for reporting, archival, or automated damage repair cost estimation.

In one embodiment, a database or other data storage device can include image data associated with a vehicle and other vehicle-related information, including but not limited to images, damage assessments, and estimated repair costs. An embodiment of the system 300 can make some or all of this information available to a remote client and user, such as 330 and 332, respectively, as the information is obtained from a field unit, such as 308a, and stored by a vehicle inspection engine 322. In some instances, information from multiple field sites and local computers, such as 304a-n, can be received, stored, and processed by a vehicle inspection engine 322 and associated database 324 or data storage device.

The system 300 can display one or more simultaneously captured images associated with a vehicle via an output device associated with a remote computer 334. In one embodiment, image data associated with a vehicle or vehicle-related image information such as simultaneously captured image information associated with a vehicle can be displayed on an output device, such as 334, associated with a remotely located client device, such as 330. Suitable types of output devices can include, but are not limited to, private-type displays, public-type displays, plasma displays, LCD displays, touch screen devices, and projector displays on cinema-type screens.

In another embodiment, a vehicle inspection engine 341 operating on a server 336 or local computer 304a-n can provide interactive functionality to prompt a remote user, such as 332, to select commands or enter text via a keypad (not shown) associated with a remotely located local computer 304a-n. Upon receipt of one or more commands or text from the remotely located local computer 304a-n, the vehicle inspection engine 341 can provide image data processing-type functionality to permit the user 332 to retrieve, view, or edit previously stored image data associated with a vehicle and other vehicle-related information. The vehicle inspection engine 341 can retrieve previously stored image data associated with a vehicle or other vehicle-related information from memory 320a-n, a database 324 or other data storage device, and provide a display or other output of some or all of the image data associated with a vehicle or other vehicle-related information.

In yet another embodiment, a vehicle inspection engine 341 operating on a server 336 or local computer 304a-n is capable providing a remote user, such as 332, the capability to utilize image data associated with a vehicle or other vehicle-related information in a document, spreadsheet, form, or other format. For example, when image data associated with a vehicle or other vehicle-related information is available for a particular user, a notification can be displayed on an output device such as 334. The notification can be formatted as an e-mail, message, or other type of communication obtainable from a website. When the user views the notification on the output device, the user can retrieve image data associated with a vehicle or other vehicle-related data, and format the data into an advertisement or a communication to offer the vehicle for sale. For example, the vehicle inspection engine 341 can provide a series of interactive Web pages for a user to display and post image data associated with a vehicle or other vehicle-related data. The Web pages can be formatted to display characteristics of the vehicle that may be of interest to a potential consumer or purchaser of the vehicle.

In one embodiment, a vehicle inspection engine 341 operating on a server 336 or local computer 304a-n can provide interactive functionality, such a website and Web pages, for a user to obtain previously captured images of a vehicle, and facilitate offering the vehicle for sale via a network such as the Internet. For instance, image data associated with a user's vehicle can be simultaneously captured by a series of image capturing devices associated with a vehicle inspection engine. Other vehicle-related information, such as VIN number and other physical characteristics, can be collected or otherwise received by the vehicle inspection engine from the user or by one or more sensors or other data collection devices, techniques, or methods. The vehicle inspection engine can then store the image data and vehicle-related information, and provide a series of one or more interactive Web pages via a website for a user to access, edit, and review the image data and vehicle-related information. Using one or more predefined forms, the vehicle inspection engine can prompt a user to input via a local computer any other information necessary to offer the vehicle of interest for sale via a network such as the Internet. In some instances, the previously collected image data and vehicle-related information may be sufficient for the vehicle inspection engine to generate an offer for sale of the vehicle of interest and post the offer, image data, and vehicle-related information on a webpage for access and review by other users or consumers who may be interested in purchasing the vehicle.

One embodiment of a vehicle inspection engine can include a main application program process with multiple threads. Another embodiment of a vehicle inspection engine can include different functional modules. An example of one programming thread or functional module can be a beam sensor detection thread or module with one signal per beam sensor. Another programming thread or module can provide physical controls such as lighting, door operations, etc. Yet another programming thread or module can provide camera control or control of one or more image capturing devices. One other programming thread or module can provide database management functionality, including storing, searching, and retrieving data, information, or data records from a combination of databases, data storage devices, and one or more associated servers.

Figure 4:
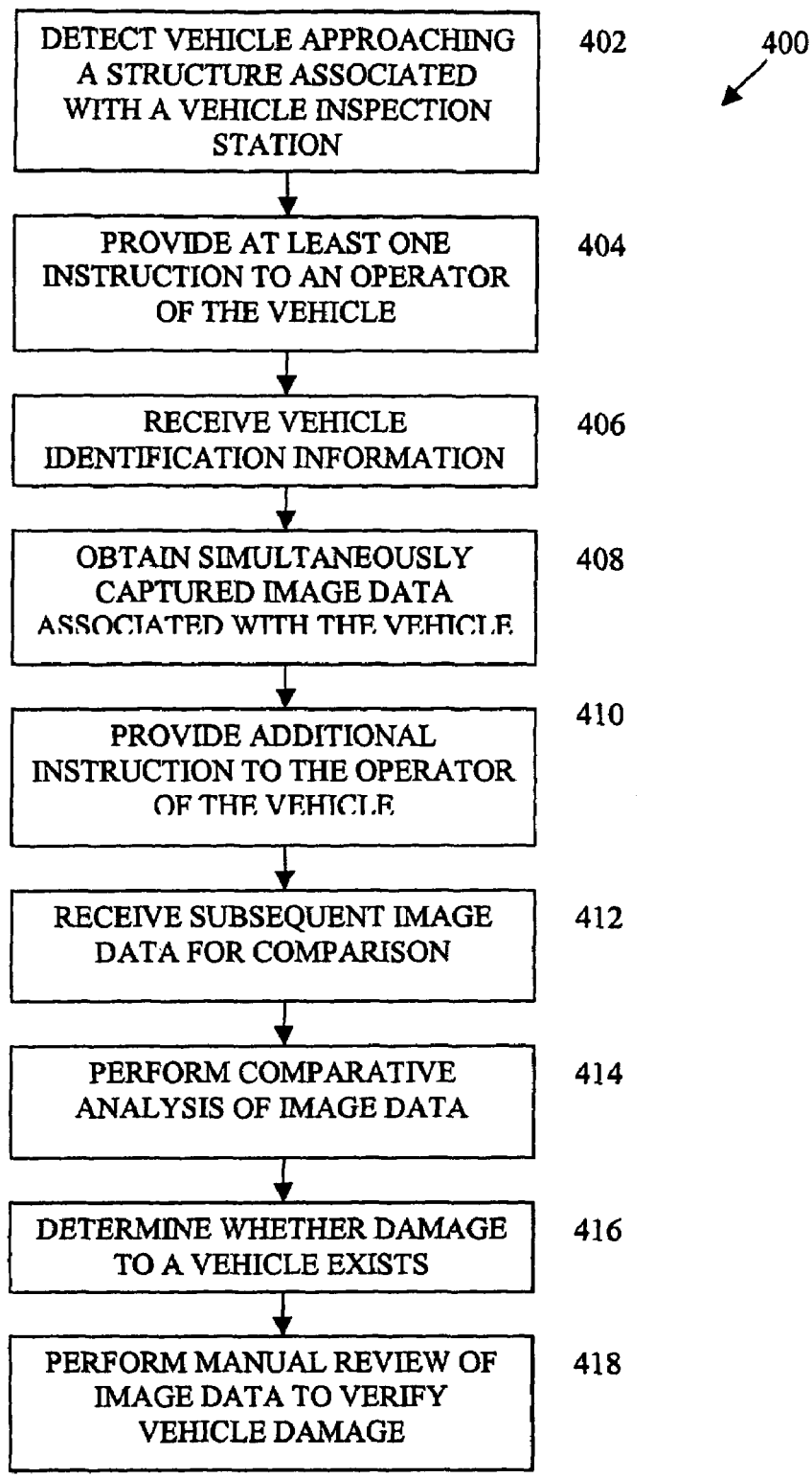
FIG. 4 is a flowchart diagram of an exemplary process in accordance with an embodiment of the invention.

FIG. 4 illustrates an exemplary process that can be implemented with a vehicle inspection station in accordance with embodiments of the invention. The process 400 shown can provide vehicle damage information to a user, person, or an interested party. Other processes can include fewer or greater elements or steps in accordance with embodiments of the invention. Yet other processes can be implemented with other embodiments of the invention. The process 400 shown in FIG. 4 begins at block 402.

At block 402, a vehicle is detected approaching a structure associated with a vehicle inspection system. In the embodiment shown in FIG. 4, a driver or operator of a vehicle, such as 306 in FIG. 3, can be instructed to approach a field unit, such as 308a in FIG. 3. As described above, the field unit 308a can enclose or otherwise protect some or all components of a vehicle inspection station, such as 301a in FIG. 3. As the vehicle 300 approaches and enters the field unit 308a, the vehicle inspection station 301a can detect the position of the vehicle 306 via one or more position sensors associated with the vehicle inspection station 301a. In one example, a position sensor can be infrared beam-type device. Other examples of position sensors are described above with respect to FIG. 3.

Block 402 is followed by block 404, in which at least one instruction is provided to an operator of the vehicle. In this embodiment, the vehicle inspection station 301a can receive a signal associated with the position of the vehicle 306 via at least one position sensor, and based in part on at least the signal, the vehicle inspection station 301a can determine the position of the vehicle 306 with respect to the field unit 308a. The vehicle inspection station 301a can generate a corresponding signal associated with one or more instructions capable of guiding a driver or operator of the vehicle 306 into and positioning the vehicle 306 adjacent to or within the field unit 308a. A driver or operator of the vehicle 306 can receive an instruction from the system 300 via one or more guide devices, such as 314a, or traffic control lighting associated with the vehicle inspection station 301a. For example, a guide device 314a can be a traffic control signal with a series of lights. Other examples of guide devices are described above with respect to FIG. 3. In this particular example, when one particular light of a traffic control signal is activated or lit, this can be an instruction for the driver or operator of the vehicle 306 to drive the vehicle 306 forward adjacent or into the field unit 308a. As the vehicle 306 enters the field unit 308a, the vehicle inspection station 301a can detect via at least one position sensor when the vehicle 306 is sufficiently positioned with respect to the field unit 308a, i.e. relative to a series of image capturing devices such as 310a. In some instances, the vehicle inspection station 301a can provide an instruction to the driver or operator of the vehicle 306 to slow down or to be ready to stop when the vehicle 306 nears a particular position or location with respect to the field unit 308a. When the vehicle 306 is sufficiently positioned, the vehicle inspection station 301a can activate another light to provide another instruction for the driver or operator of the vehicle 306 to stop the vehicle 306 adjacent to or within the field unit 308a. Some or all of the functions of blocks 402 and 404 can be repeated as necessary until a vehicle is sufficiently positioned with respect to the field unit 308a and/or to a series of image capturing devices 310a.

Block 404 is followed by block 406, in which vehicle identification information is received. In some embodiments, this element and functionality is optional. When the vehicle is sufficiently positioned with respect to the field unit 308a, or to a series of image capturing devices 310a, and adjacent to a vehicle identification device, the a series of image capturing devices 310a can identify the vehicle, such as 306. In the embodiment shown, the vehicle inspection station 301a can receive a signal from a vehicle identification device, such as 316a, for instance, a bar code reader or RFID tag reader. Other examples of vehicle identification devices or techniques, routines, or processes are described in greater detail above in FIG. 3. For example, a vehicle identification device such as 316a can be mounted to or adjacent to the field unit 308a, and the vehicle identification device 316a can transmit a signal with vehicle identification information to or the system 300 while the vehicle 306 is adjacent to or within the field unit 308a. Based at least in part on the vehicle identification information, the vehicle inspection station 301a can identify the vehicle. In some instances, a vehicle of interest may be identified as "new vehicle to the system" and the vehicle inspection station 301a can generate a data record or other data with the vehicle identification information for storage in a database, such as 324, or data storage device. In other instances, a vehicle of interest may be identified as a "return vehicle to the system," and the vehicle inspection station 301a can retrieve corresponding data records or other data with any previously stored or prior vehicle identification information from an associated database 324 or data storage device.

In one embodiment, the vehicle identification device can be a bar code reader. If a vehicle of interest includes a bar code with vehicle identification information, the bar code can be read automatically or manually by a vehicle identification device. The bar code reader can then generate a signal associated with the vehicle identification information, and the signal can be transmitted to the vehicle inspection station 301a for processing. When the vehicle inspection station 301a receives the signal, the vehicle inspection station 301a can process the signal to obtain the vehicle identification information and to identify the vehicle. In some instances, the vehicle inspection station 301a may access a database, such as 324, or other data storage device, and compare vehicle identification information to previously stored data. If no corresponding vehicle identification information exists in the associated database 324 or data storage device, the vehicle inspection station 301a can add the information to the database 324 or data storage device. If corresponding vehicle identification information exists in the database 324 or data storage device, the vehicle inspection station 301a can retrieve such corresponding information and add, update, or edit any new vehicle identification information to an associated data record in the database 324 or data storage device.

Other types of data such as vehicle-related data, position data, vehicle identification data, or other data associated with a vehicle can be collected or otherwise received by processes, routines, software, or inspection devices such as sensors associated with a vehicle inspection station, such as 301a. Any associated signals from such processes, routines, software, or inspection devices can be transmitted to or received by other components associated with the vehicle inspection station 301a. Similar to the data examples above, these types of data can be stored for subsequent retrieval or processing.

Block 406 is followed by block 408, in which simultaneously captured image data associated with the vehicle is obtained. When the vehicle 306 is sufficiently positioned with respect to the field unit 308a and adjacent to a set of image capturing devices, the vehicle inspection station 301a can obtai simultaneously captured image data. In this embodiment, the vehicle inspection station 301a can initiate a set of computer-executable instructions, such as a vehicle inspection application program, capable of simultaneously capturing image data associated with a vehicle. In this example, a series of image capturing devices, such as 310a or cameras, can be mounted to or adjacent to the field unit 308a, and can be operated and controlled by the vehicle inspection station 301a. Examples of image capturing devices are described in greater detail above with respect to FIG. 3. The image capturing devices 310a can obtain or otherwise receive simultaneously captured image data associated with the vehicle 306, and transmit the image data to other components associated with the vehicle inspection station 301a, such as a database, for instance 324, or other data storage device. The image data can be stored for subsequent retrieval or processing.

In the embodiment shown, the vehicle inspection station 301a can associate collected image data for a particular vehicle with some or all corresponding vehicle identification information in memory such as 320a, an associated database such as 324, or other associated data storage device. When some or all of the image data is stored, the process 400 can continue.

Block 408 is followed by block 410, in which an additional instruction is provided to the operator of the vehicle. In some embodiments, this element and functionality is optional. After simultaneously captured image data associated with the vehicle 306 is obtained or received by the vehicle inspection station 301a, the vehicle inspection station 301a can provide an instruction to the driver or operator of the vehicle 306 to drive away from the field unit 308a. Continuing the example provided above, yet another light of an associated traffic control signal, or guide device 314a, can be activated by the vehicle inspection station 301a to instruct the driver or operator of vehicle 306 that the vehicle 306 can be driven away from the field unit 308a.

Block 410 is followed by block 412, in which subsequent image data associated with the vehicle is received for comparison. In some embodiments, this element and functionality is optional. If a vehicle, such as 306, incurs or otherwise becomes damaged, the vehicle can return to the field unit 308a associated with a vehicle inspection station 301a, or to another field unit associated with another vehicle inspection station and associated with the same vehicle inspection system 300. In some instances, damage to a vehicle, such as 306, can occur by collision with an object, such as another vehicle, or may occur over time. The process and system embodiments disclosed herein are not limited to detecting and identifying damage to a vehicle, but can include detecting and identifying repairs or any other change to a physical characteristic of a vehicle. Similar to the process and functionality described above for blocks 400 through 408, the vehicle 306 can be positioned relative to a field unit 308a associated with a vehicle inspection station, such as 301a, or to another field unit associated another vehicle inspection station and associated with the vehicle inspection system 300. Simultaneously captured image data associated with the vehicle is obtained by the vehicle inspection station, such as 301a, via the series image capturing devices, such as 310a. The simultaneously captured image data can then be stored in a memory such as 320a, database such as 324, or data storage device. Other data such as vehicle-related information or vehicle identification data can also be obtained by the vehicle inspection station 301a and stored in the memory such as 320a, database such as 324, or data storage device. After image data or other vehicle-related data is transmitted to the vehicle inspection station 301a, the vehicle inspection station 301a can provide instructions for the driver or operator of the vehicle 306 to drive away from the field unit 308a.

Block 412 is followed by block 414 in which a comparative analysis of image data is performed. In the embodiment shown, the vehicle inspection station 301a can begin an automated comparison and analysis of image data. Comparative techniques and/or pattern recognition software or devices can be used to compare prior image data associated with a vehicle with subsequent image data associated with the vehicle. Suitable comparative techniques and/or pattern recognition software or devices in accordance with embodiments of the invention can determine a similarity between at least two images, a dissimilarity between at least two images, dirt, a dent, a scratch, a color, a paint imperfection, a body imperfection, or a pattern. In one embodiment, a vehicle inspection station 301a can perform a bit by bit comparison between two digital-type images. Other techniques, software, or devices can be utilized in accordance with other embodiments of the invention.

Block 414 is followed by decision block 416, in which a determination is made whether damage to a vehicle exists. If the vehicle inspection station 301a identifies potential damage to or a change in a physical characteristic of the vehicle 306, the vehicle inspection station 301a can provide a notification to a user that particular image data or information should be reviewed further, either manually or by automation. If upon further review of the image data or information, damage to or a change in a physical characteristic of the vehicle 306 is identified, then the vehicle inspection station 301a can automatically provide a notification to a user or a report for a user can automatically be generated. Such notifications and reports can be sent to a user, such as a customer, an estimator, a vehicle owner, a vehicle dealer, or other person with an interest in the particular vehicle.

Block 416 is followed by block 418, in which a manual review of image data is performed, and vehicle damage is identified. In some embodiments, this element and functionality is optional. In this embodiment, a remote user such as 332 in FIG. 3 can operate a remote client 330 to access, view, and analyze data collected and stored by the vehicle inspection station 301a. For example, a user 332 may receive a notification from the vehicle inspection station 301a that a damage report has been generated. The user 332 can access the remote client 330 to obtain the damage report from the vehicle inspection station 301a. The vehicle inspection station 301a via a vehicle inspection engine, such as 322a, can provide user interface functionality, such as a website with associated Web pages, to interact with a user and to provide additional functionality to access, view, or analyze the data collected and stored by the vehicle inspection station 301a in memory such as 320a, an associated database such as 324, or other associated data storage device. In one embodiment, a remote client such as 330 can include an output device such as a display screen, and the remote client 330 can be in communication with a vehicle inspection station 301a via a network. Via the remote client 330, the user 332 can manually review and analyze some or all image data collected by the vehicle inspection station 301a for a particular vehicle. In some embodiments, the user 332 can physically inspect the vehicle of interest to verify whether identified damage exists. In other embodiments, the user 332 can verify via image data whether identified damage exists. In either instance, the user 332 can edit, delete, or enter additional vehicle-related information to be collected and stored by the vehicle inspection station 301a in memory such as 320a, an associated database such as 324, or other associated data storage device. In this manner, image data associated with a vehicle, vehicle-related information and/or other information associated with a vehicle and collected by a vehicle inspection station, such as 301a, can be used in conjunction with vehicle-related information collected by a user, such as 332, to generate reports or other types of communications or notifications regarding vehicle damage, repairs, or changes to a physical characteristic to a vehicle of interest.

The process 400 ends at block 418.

Figure 5:
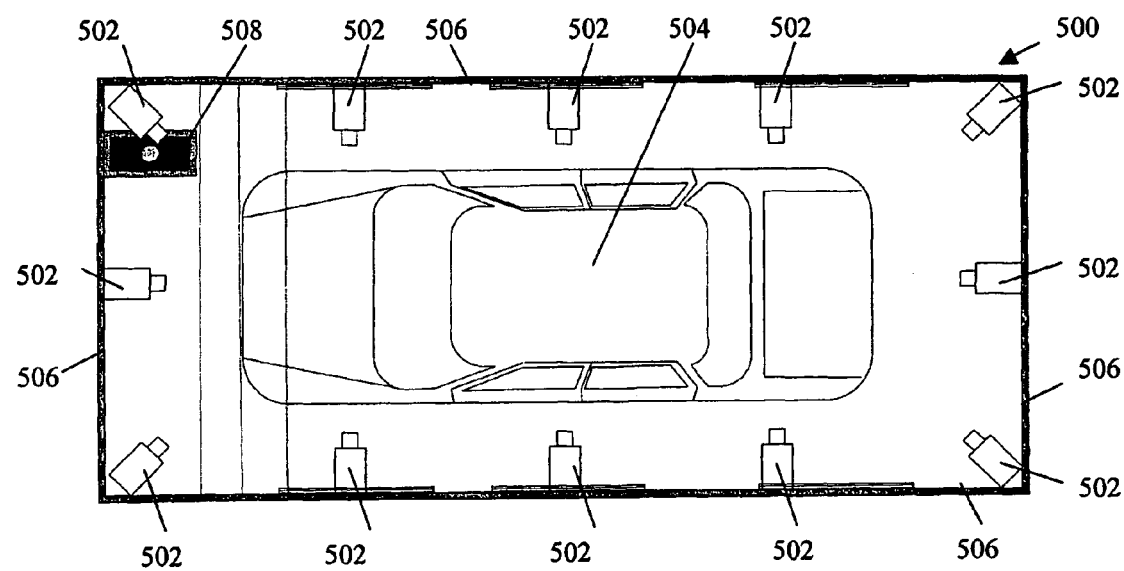
FIG. 5 is an exemplary arrangement of image capturing devices for a single vehicle inspection station in accordance with an embodiment of the invention.

FIG. 5 is exemplary arrangement of image capturing devices for a vehicle inspection station in accordance with an embodiment of the invention. The view shown in FIG. 5 is an overhead view 500 of multiple image capturing devices 502 positioned adjacent to a vehicle 504 of interest. In this example, twelve image capturing devices or cameras can obtain respective angles or views of the vehicle 504 of interest. Each of the image capturing devices 502 are shown positioned adjacent to and mounted the interior of a structure or field unit 506. A guide device 508, in this example, a three light traffic control indicator, can mount to a portion of the structure or field unit 506 for observation by a driver or operator of the vehicle 504. Other aspects and functionality of the image capturing devices 502, field unit 506, and guide device 508 are described above in FIG. 3.

Figure 6:
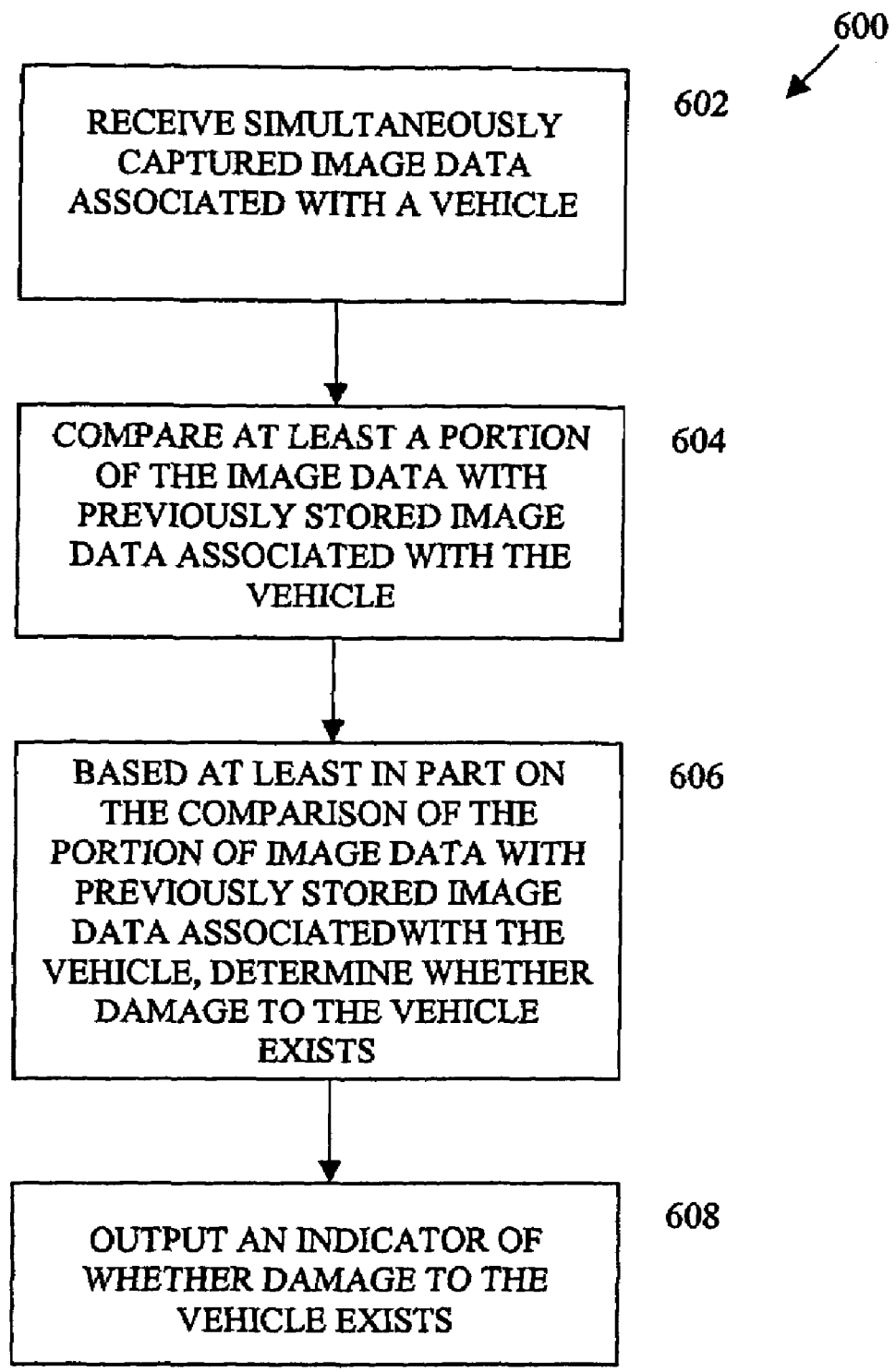
FIG. 6 is a flowchart diagram of another exemplary process in accordance with an embodiment of the invention.

FIG. 6 is a flowchart for an exemplary method in accordance with an embodiment of the invention. The method 600 shown can provide vehicle damage information to an interested party. The method 600 can be implemented by the system 300 in FIG. 3. Other methods in accordance with embodiments of the invention can have fewer or additional steps than the method 600 described below.

The method 600 begins in block 602. In block 602, simultaneously captured image data associated with a vehicle is received. In the embodiment shown, a vehicle inspection engine, such as 322a in FIG. 3, can receive simultaneously captured image data associated with a vehicle, such as 306, from a series of image capturing devices, such as 310a in FIG. 3. When a vehicle 306 is sufficiently positioned adjacent to a series of image capturing devices 310a, the vehicle inspection engine 322a can activate the series of image capturing devices 310a to obtain simultaneously captured image data associated with the vehicle 306. For example, a series of twelve cameras in a vehicle inspection station can obtain and transmit simultaneously captured image data associated with a vehicle such as 306.

Block 602 is followed by block 604, in which at least a portion of the image data is compared with previously stored image data associated with the vehicle. In the embodiment shown, a vehicle inspection engine, such as 322a in FIG. 3, can compare previously stored image data with some or all of the simultaneously captured image data associated with a vehicle, such as 306. For example, a conventional image comparison and/or a pattern recognition technique, routine, software or device can be used to compare at least two images.

Block 604 is followed by block 606, in which based at least in part on the comparison of the portion of image data with previously stored image data associated with the vehicle, a determination is made whether damage to the vehicle exists. In the embodiment shown, a vehicle inspection engine, such as 322a in FIG. 3, can compare previously stored image data with some or all of the simultaneously captured image data associated with a vehicle, such as 306, utilizing a conventional image comparison and/or pattern recognition technique, routine, software or device can be used to compare at least two images. If the vehicle inspection engine 322a detects at least one difference between the at least one previously stored image and at least one corresponding subsequently captured image, then the vehicle inspection engine can determine that damage exists to the vehicle. Damage can include any change in a physical characteristic to a vehicle.

Block 606 is followed by block 608, in which an indicator of whether damage to the vehicle exists is output. In the embodiment shown, a vehicle inspection engine, such as 322a in FIG. 3, can generate an output such as a notification to a user if damage to the vehicle, such as 306, exists. For example, an output can be a report, e-mail, message, display, image, or any other communication or output capable of informing a user if damage to a particular vehicle of interest exists.

The method 600 ends at block 608.

Figure 7:
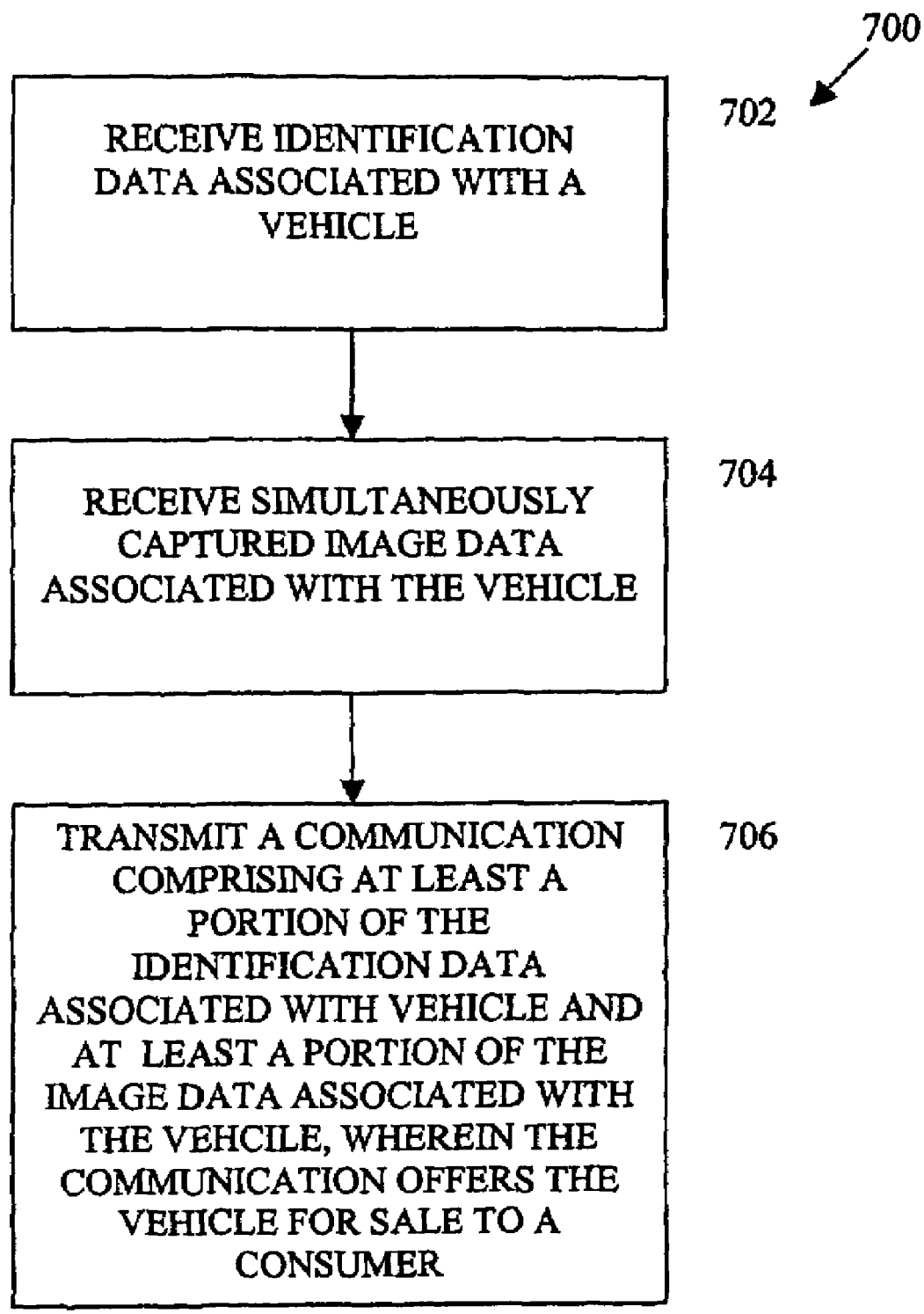
FIG. 7 is a flowchart diagram of another exemplary process in accordance with an embodiment of the invention.

FIG. 7 is a flowchart for another method in accordance with an embodiment of the invention. The method 700 shown can provide a method for offering a vehicle for sale. The method 700 can be implemented by the system 300 shown in FIG. 3. Other methods in accordance with embodiments of the invention can have fewer or additional steps than the method 700 described below.

The method 700 begins in block 702. In block 702, identification data associated with a vehicle is received. In the embodiment shown, a vehicle inspection engine, such as 322a in FIG. 3, can receive vehicle identification data or other vehicle-related information associated with a vehicle, such as 306, from a identification device, such as 316a in FIG. 3. When a vehicle 306 is positioned adjacent to a identification device 316a, the vehicle inspection engine 322a can activate or otherwise operate the identification device 316a to obtain vehicle identification information or other vehicle-related information associated with the vehicle 306. For example, an identification device can be a bar code reader or a RFID reader device. When a bar code or RFID associated with the vehicle 306 is read by a respective bar code reader or a RFID reader device, vehicle identification information can be obtained or otherwise derived from the bar code or RFID.

Block 702 is followed by block 704, in which simultaneously captured image data associated with the vehicle is received. In the embodiment shown, the vehicle inspection engine 322a can receive simultaneously captured image data associated with a vehicle 306, from a series of image capturing devices, such as 310a in FIG. 3. When a vehicle 306 is sufficiently positioned adjacent to a series of image capturing devices 310a, the vehicle inspection engine 322a can activate the series of image capturing devices 310a to obtain simultaneously captured image data associated with the vehicle 306.

Block 704 is followed by block 706, in which a communication comprising at least a portion of the identification data associated with the vehicle and at least a portion of the image data associated with the vehicle is transmitted, wherein the communication offers the vehicle for sale to a consumer. In the embodiment shown, the vehicle inspection engine 322a can format and combine the vehicle identification information or other vehicle-related information associated with the vehicle 306 and some or all of the simultaneously captured image data associated with a vehicle 306 into a communication, such as a report, e-mail, a message, display, image, or any other communication or output capable of offering the vehicle for sale. Such communications can include a price the vehicle will be or is offered for sale. The communication can be posted, sent, or otherwise transmitted to any number of parties via a network, mail, or other communication techniques, routines, or devices.

The method 700 ends at block 706.

While the above description contains many specifics, these specifics should not be construed as limitations on the scope of the invention, but merely as exemplifications of the disclosed embodiments. Those skilled in the art will envision many other possible variations that within the scope of the invention as defined by the claims appended hereto.

The invention claimed is:

1. A method for providing vehicle damage information to an interested party, comprising:
   receiving simultaneously captured image data associated with a vehicle;
   comparing at least a portion of the image data with previously stored image data associated with the vehicle;
   based at least in part on the comparison of the portion of image data with previously stored image data associated with the vehicle, determining whether damage to the vehicle exists; and
   outputting an indicator of whether damage to the vehicle exists.

2. The method of claim 1, further comprising:
   positioning a vehicle adjacent to a plurality of image capturing devices capable of simultaneously capturing a plurality of images of the vehicle.

3. The method of claim 2, further comprising:
   sensing a position associated with the vehicle; and
   providing at least one instruction to an operator of the vehicle to position the vehicle with respect to the plurality of image capturing devices capable of simultaneously capturing a plurality of images of the vehicle.

4. The method of claim 1, further comprising:
   receiving identification data associated with the vehicle;
   associating the image data with the identification data associated with the vehicle; and
   based at least in part on the identification data associated with the vehicle, locating previously stored image data associated with the vehicle.

5. The method of claim 4, wherein the identification data comprises at least one of the following: a vehicle identification number, a license plate, a dealer tag, vehicle-related data from a radio frequency identification device, vehicle-related data from a bar code, a vehicle make, a vehicle model, or a vehicle year of manufacture.

6. The method of claim 1, wherein receiving simultaneously captured image data associated with the vehicle comprises receiving a plurality of images of the vehicle from a plurality of image capturing devices.

7. The method of claim 1, wherein receiving simultaneously captured image data associated with the vehicle comprises receiving near-simultaneously captured images from at least one image capturing device.

8. The method of claim 1, wherein comparing at least a portion of the image data with previously stored image data associated with the vehicle comprises comparing the portion of the image data with at least one image of the vehicle obtained earlier than the image data.

9. The method of claim 1, wherein comparing at least a portion of the image data with previously stored image data associated with the vehicle comprises comparing the portion of image data with at least one image associated with a standard set of images of the vehicle.

10. The method of claim 1, wherein determining whether damage to the vehicle exists comprises identifying at least one of the following: a similarity between at least two images, a dissimilarity between at least two images, dirt, a dent, a scratch, a color, a paint imperfection, a body imperfection, or a pattern.

11. The method of claim 1, wherein outputting an indicator of whether damage to the vehicle exists comprises at least one of the following: displaying at least one image of the damage to the vehicle, generating a report of the damage, or transmitting a signal to notify a person that damage to the vehicle exists.

12. A system for identifying damage to a vehicle and providing damage-related information to an interested party, comprising:
    a plurality of image capturing devices capable of simultaneously capturing image data of a vehicle;
    a vehicle inspection engine capable of
        receiving from the plurality of image capturing devices simultaneously captured image data associated with the vehicle;
        comparing at least a portion of the image data with previously stored image data associated with the vehicle;
        based at least in part on the comparison of the image data with previously stored image data associated with the vehicle, determining whether damage to the vehicle exist; and
        outputting an indicator of whether damage to the vehicle exists.

13. The system of claim 12, wherein the vehicle inspection engine is further capable of:
    receiving identification data associated with a vehicle;
    associating the image data with the identification data associated with the vehicle; and
    based at least in part on the identification data associated with the vehicle, locating previously stored image data associated with the vehicle.

14. The system of claim 12, further comprising:
    at least one sensor adapted to detect a position associated with the vehicle; and
    at least one indicator adapted to provide at least one instruction to an operator of the vehicle to position the vehicle with respect to the plurality of image capturing devices.

15. The system of claim 12, further comprising
    an enclosure adapted to
        receive a vehicle; and
        mount the plurality of image capturing devices, the at least one sensor adapted to detect a position associated with the vehicle, and the at least one indicator adapted to provide at least one instruction to an operator of the vehicle to position the vehicle with respect to the plurality of image capturing devices with respect to the vehicle.

16. A computer-readable medium containing program code, comprising:
    program code for receiving simultaneously captured image data associated with a vehicle;
    program code for comparing at least a portion of the image data with previously stored image data associated with the vehicle;
    program code for determining whether damage to the vehicle exists based at least in part on the comparison of the portion of image data with previously stored image data associated with the vehicle; and
    program code for outputting an indicator of whether damage to the vehicle exists.

17. The computer readable medium of claim 16, further comprising:
    program code adapted to receive identification data associated with the vehicle;
    program code adapted to associate the image data with the identification data associated with the vehicle; and
    program code adapted to locate previously stored image data associated with the vehicle based at least in part on the identification data associated with the vehicle.

* * * * *